(12) United States Patent
Hodorek

(10) Patent No.: US 7,235,080 B2
(45) Date of Patent: Jun. 26, 2007

(54) FEMORAL REFERENCE TIBIAL CUT GUIDE

(75) Inventor: Robert A. Hodorek, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 121 days.

(21) Appl. No.: 10/370,049

(22) Filed: Feb. 20, 2003

(65) Prior Publication Data

US 2004/0167531 A1 Aug. 26, 2004

(51) Int. Cl.
*A61F 5/00* (2006.01)
(52) U.S. Cl. .................................... 606/87
(58) Field of Classification Search .......... 606/87, 606/88, 90, 53, 86, 89, 84
See application file for complete search history.

(56) References Cited

U.S. PATENT DOCUMENTS

| | | | |
|---|---|---|---|
| 3,756,242 A * | 9/1973 | Coss | 606/167 |
| 4,406,568 A * | 9/1983 | Rogers et al. | 409/182 |
| 4,524,766 A * | 6/1985 | Petersen | 606/88 |
| 4,566,448 A * | 1/1986 | Rohr, Jr. | 606/88 |
| 4,738,253 A * | 4/1988 | Buechel et al. | 606/80 |
| 4,759,350 A * | 7/1988 | Dunn et al. | 606/82 |
| 4,938,762 A * | 7/1990 | Wehrli | 606/88 |
| 5,250,050 A * | 10/1993 | Poggie et al. | 606/79 |
| 5,676,668 A * | 10/1997 | McCue et al. | 606/87 |
| 5,800,438 A * | 9/1998 | Tuke et al. | 606/90 |
| 5,860,980 A * | 1/1999 | Axelson et al. | 606/88 |
| 6,296,646 B1 | 10/2001 | Williamson | 606/90 |
| 6,344,043 B1* | 2/2002 | Pappas | 606/96 |
| 6,478,799 B1* | 11/2002 | Williamson | 606/90 |
| 6,648,896 B2* | 11/2003 | Overes et al. | 606/90 |
| 6,758,850 B2* | 7/2004 | Smith et al. | 606/88 |
| 6,770,077 B2* | 8/2004 | Van Zile et al. | 606/88 |
| 2002/0133164 A1 | 9/2002 | Williamson | 606/90 |
| 2004/0087960 A1* | 5/2004 | Kinnett | 606/88 |
| 2004/0249387 A1* | 12/2004 | Faoro | 606/88 |

OTHER PUBLICATIONS

Zimmer Inc., NEXGEN® Complete Knee Solution: Revision Instrumentation Surgical Technique for Legacy® Knee Constrained Condylar Knee, 2001, pp. 1, 7-10, 60.
Zimmer Inc., NEXGEN® Complete Knee Solution: Surgical Technique for Cruciate Retaining Knees and Revision Instrumentation Surgical Technique for Cruciate Retaining Augmentable Knees, 2002, pp. 1, 70-78, 139.

* cited by examiner

*Primary Examiner*—Anuradha Ramana
(74) *Attorney, Agent, or Firm*—Baker & Daniels LLP

(57) ABSTRACT

A femoral reference tibial cut guide for cutting the proximal tibia to receive a tibial implant. The cut guide references the femur to determine the appropriate tibial resection.

7 Claims, 3 Drawing Sheets

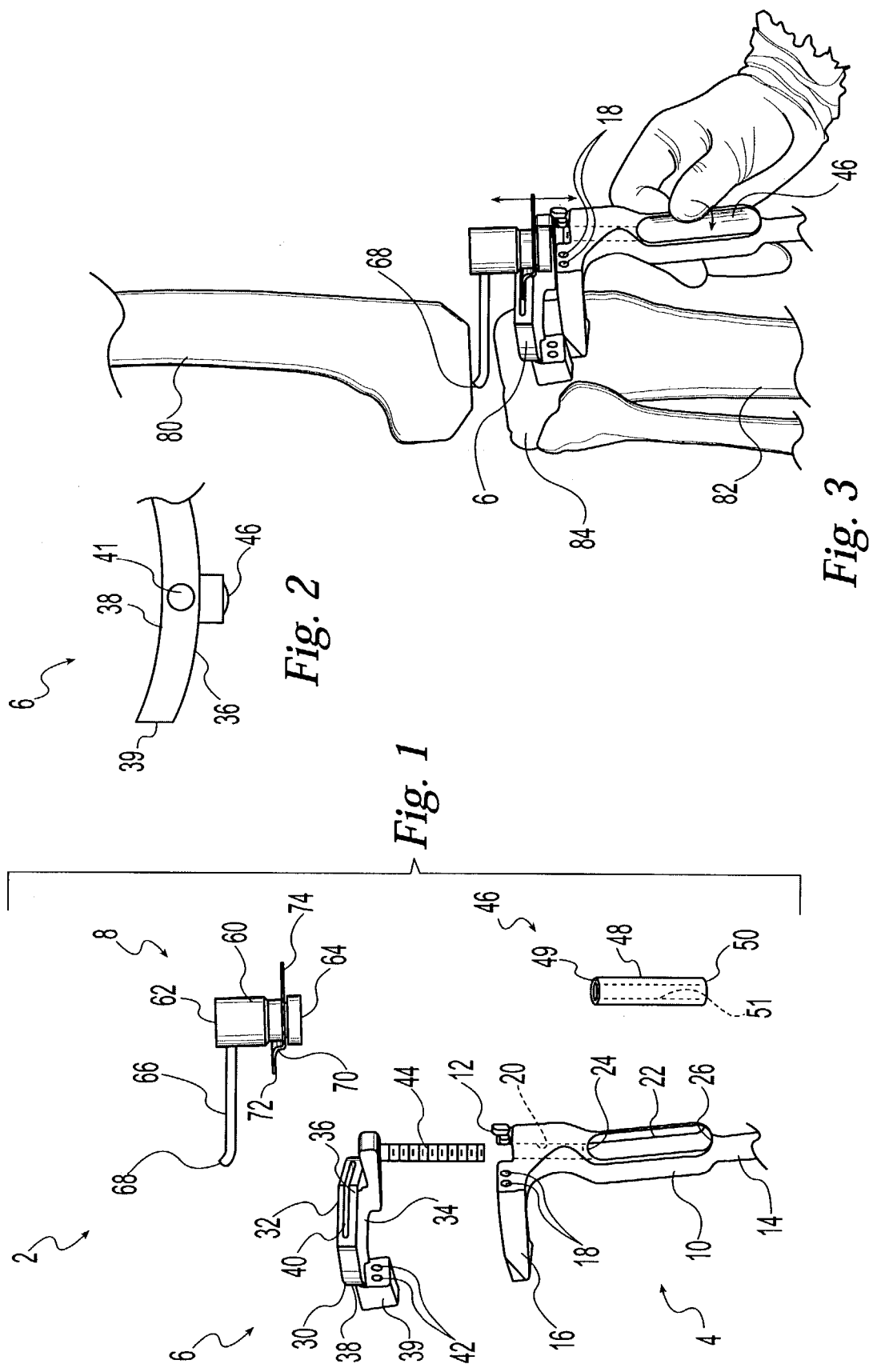

US 7,235,080 B2

FEMORAL REFERENCE TIBIAL CUT GUIDE

FIELD OF THE INVENTION

The present invention relates to a bone cutting guide, in particular to a guide for cutting the proximal tibia which establishes the tibial cut level by referencing the femur.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 1 is an exploded oblique elevation view of an illustrative tibial cut guide assembly according to the present invention.

FIG. 2 is a top plan view of the tibial cut guide assembly of FIG. 1.

FIG. 3 is an oblique elevation view of the tibial cut guide assembly of FIG. 1 positioned adjacent a knee joint in extension.

DESCRIPTION OF THE ILLUSTRATED EMBODIMENTS

Figure 4:
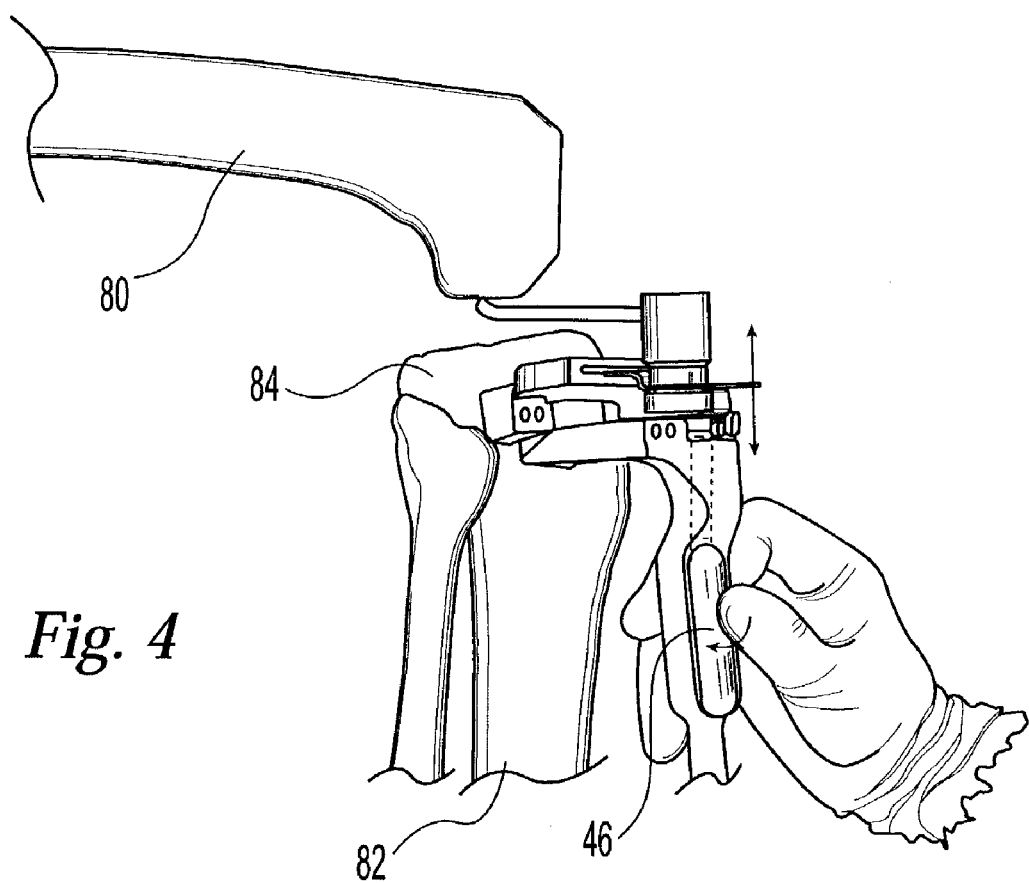
FIG. 4 is an oblique elevation view of the tibial cut guide assembly of FIG. 1 positioned adjacent a knee joint in flexion.

FIGS. 1-4 depict an illustrative tibial cut guide 2 assembly comprising a base 4, a cut head 6, and a depth reference probe 8. The base 4 includes an elongate body 10 having a proximal end 12, a distal end 14, and a longitudinal axis extending from the proximal end to the distal end. A pair of support arms 16 extends medially and laterally from the proximal end generally perpendicular to the longitudinal axis. Fixation holes 18 extend through the base 4 at the proximal end 12. A longitudinal bore 20 opens at the proximal end and extends along a portion of the longitudinal axis. A side opening 22 in the base 4 includes a top surface 24 and bottom surface 26. The longitudinal bore 20 extends through the top and bottom of the side opening 22 to communicate with the side opening 22.

The cut head 6 includes a body 30 having a proximal surface 32, a distal surface 34, an anterior side 36, a posterior side 38, a medial side 37, and a lateral side 39. A saw guide slot 40 extends through the cut head 6 from the anterior side 36 to the posterior side 38 to define a cutting plane having a downward posterior slope, typically on the order of 7°. The proximal surface 32 is parallel to the slot and can alternatively be used as a saw guiding surface offset a known distance from the slot. A mounting hole 41 extends from the proximal surface 32 down to communicate with the slot 40. Fixation holes 42 extend through the medial and lateral sides 37, 39 of the cut head body 30 directed from anterior to posterior. A threaded, elongate elevation shaft 44 extends downwardly from the distal surface 34. An adjustment knob 46 includes an elongate cylindrical body 48 having a proximal end 49, a distal end 50, and a threaded through bore 51.

The body 48 of the knob 46 is sized to fit within the side opening 22 with its through bore 51 aligned with the base through bore 20 and its proximal 49 and distal 50 ends adjacent the top 24 and bottom 26 surfaces of the side opening 22. The side of the knob 46 projects through the side opening 22 to provide access to turn the knob 46.

The cut head or cutter guide 6 is assembled to the base 4 by inserting the adjustment knob 46 into the side opening 22 and inserting the elevation shaft 44 into the longitudinal through bore 20. The adjustment knob is then threaded onto the elevation shaft 44 to retain the cut head 6 in the base 4. The cut head 6 is constrained against proximal-distal motion by the abutment of the proximal end 49 and distal end 50 of the knob 46 with the top 24 and bottom 26 of the side opening 22. Proximal-distal adjustment of the cut head is accomplished by turning the knob 46 which moves the elevation shaft 44 relative to the knob.

A depth reference probe 8 includes a cylindrical body 60 having a proximal end 62, a distal end 64, and a longitudinal axis extending from the proximal end 62 to the distal end 64. A probe arm 66 extends from the body 60 adjacent the proximal end 62 generally perpendicular to the body axis. The arm 66 terminates at an upturned probe tip 68. An engagement tab 70 extends from the body 60 adjacent the distal end 64 generally perpendicular to the body axis. The tab 70 is double ended, having a first end 72 spaced a first axial distance from the probe tip 68 and a second end 74 spaced a second axial distance from the probe tip 68 as measured along the longitudinal axis of the body 60. Each end is marked with the tibial implant thickness required to restore the knee to the spacing existing at the time the probe is used to position the tibial cut guide. The engagement tab 70 is mounted on the body 60 for rotation about the longitudinal axis so that the first and second ends 72, 74 can be alternately positioned on the same side of the body as the probe tip 68. The first and second ends 72, 74 of the engagement tab 70 are sized to fit within the saw guide slot 40.

FIG. 3 shows the cut guide assembly in process of being mounted adjacent a knee joint including a femur 80 and a tibia 82. The base 4 is positioned adjacent the proximal end 84 of the tibia 82 with the support arms 16 in contact with the tibia and the longitudinal base axis parallel to the tibial bone axis. Fixation pins are inserted through the base fixation holes 18 to anchor the base 4 in position. The knee is placed in zero degrees of flexion and the bones are distracted to the extent permitted by the soft tissues surrounding the joint. Distraction can be accomplished by using a retractor, by using traction, or by other suitable means. The adjustment knob 46 is turned to move the cut head and probe tip 68 up until the tip 68 contacts the distal femoral bone. This sets the tibial resection level to a known distance from the femoral bone.

Tibial implants are typically provided as one-piece or two-piece constructs. The probe 8 is sized to correspond to the available total tibial implant thicknesses so that when the tibia 82 is cut, the surgeon is assured that there is a tibial implant with a total thickness that will exactly replace the cut bone and reproduce the joint spacing and soft tissue tension that existed at the time the probe adjustment was made. When the probe 8 is to be used with a femur 80 that has already been cut to receive a femoral implant, as shown in FIG. 2, the probe spacing includes the thickness of the femoral implant as well as the thickness of the tibial implant. However, femoral implants are typically designed to replace the same amount of bone regardless of size, so only the tibial implant thickness needs to be shown on the probe 8. When the probe 8 is to be used with an uncut femur, the probe spacing corresponds to the thickness of the tibial implant. Each probe 8 can have two spacings that are alternatively selectable as shown in the illustrative embodiment and multiple probes can be provided that correspond to a variety of possible implant thicknesses.

After the desired resection level is set, fixation pins are inserted through the cut head fixation holes 42 to fix the cut head 6 in position. The probe 8 is removed and a saw blade is activated through the saw slot 40 to cut the proximal tibia 84 at the desired level. The cut head 6 and base 4 are then removed and the implants inserted.

In addition to setting the resection level with the knee in zero degrees of flexion, the tibial cut guide assembly can be used at other flexion positions between zero degrees and full flexion. FIG. 4 shows the illustrative cut guide assembly 2 mounted on the knee in approximately ninety degrees of flexion. The resection level is set as described above. Furthermore, after the resection level is set at one angle of knee flexion, the knee can be repositioned and compared to the cut guide assembly to see if the same resection level will suffice for the new position. If not, the soft tissues constraining the knee joint can be selectively cut to balance the resection level at different flexion angles. The resection level can also be adjusted to a compromise position.

Figure 5:
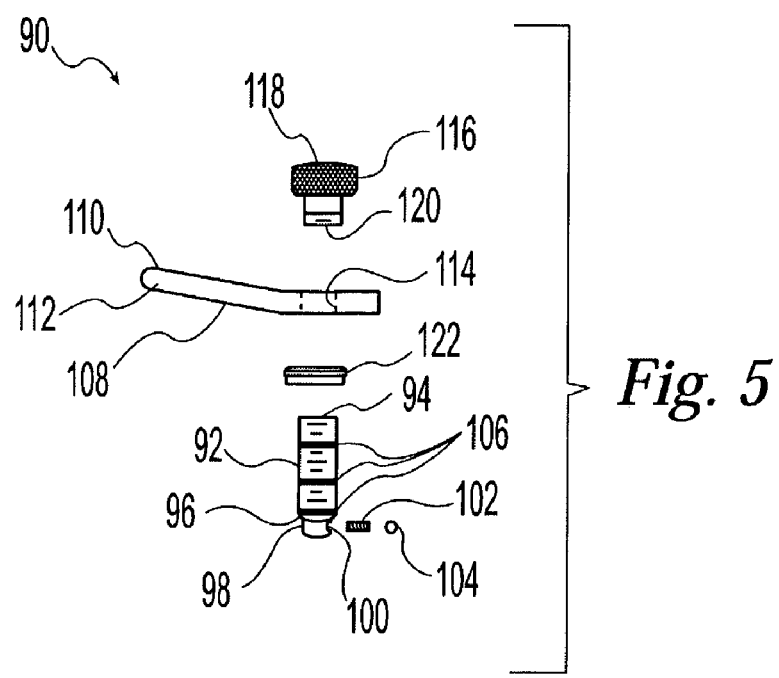
FIG. 5 is an exploded side elevation view of an alternative illustrative embodiment of a depth reference probe.
Figure 6:
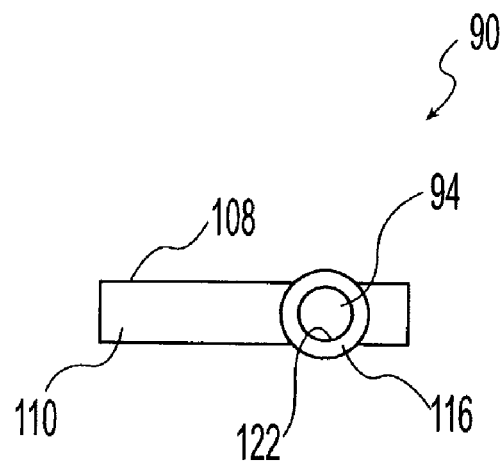
FIG. 6 is a top plan view of the alternative depth reference probe of FIG. 5.
Figure 7:
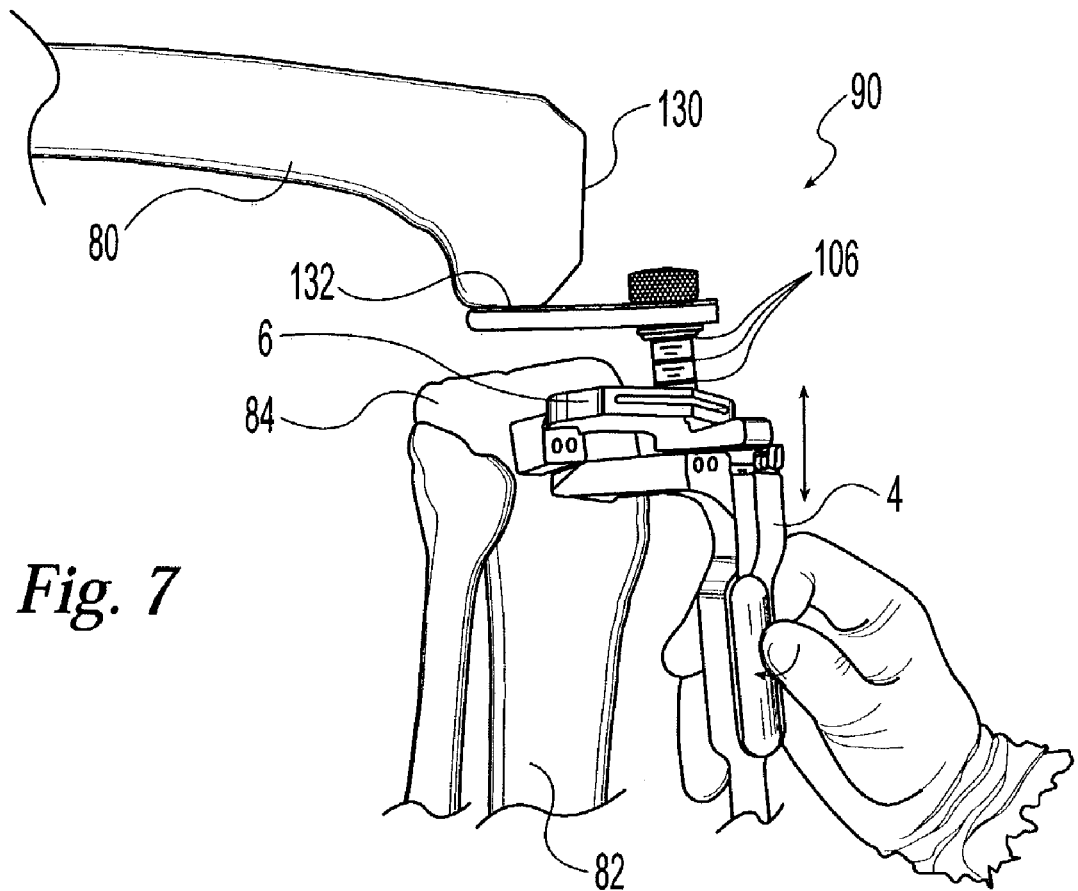
FIG. 7 is an oblique elevation view of the alternative depth reference probe mounted on the cut guide of FIG. 1 and positioned adjacent a knee joint in flexion.

FIGS. 5-7 show an alternative illustrative embodiment of a probe 90. The probe 90 includes a threaded, elongate shaft 92 having a proximal end 94, a distal end 96, and a longitudinal axis from the proximal end 94 to the distal end 96. A cut guide engaging portion 98 is formed adjacent the distal end 96 and includes a bore 100 containing a spring 102 and a ball 104. Size indicia or marks 106 corresponding to the available total tibial implant thicknesses are spaced along the shaft. A probe blade 108 includes a flat upper surface 110, a lower surface 112, and a through hole 114 from the upper surface to the lower surface. A knob 116 comprises a cylindrical body having a proximal end 118, a distal end 120, and a longitudinal axis from the proximal end 118 to the distal end 120. A threaded, axial through bore extends through the knob 116 from the proximal end 118 to the distal end 120. The exterior of the knob 116 is threaded adjacent the distal end 120. The externally threaded portion of the knob fits through the hole 114 in the blade and is held in place by a nut 122 threaded onto the distal end of the knob 116. After tightening the nut 122, the knob 116 remains rotatable relative to the blade 108. The knob 118 is threadably received on the shaft 92 such that by turning the knob relative to the shaft 92 and blade 108, the blade 108 can be positioned up and down on the shaft. The implant thickness setting is read by noting which mark 106 is adjacent the nut 122.

In use, the probe 90 is mounted on the cut head 6 by inserting the cut guide engaging portion 98 into the mounting hole 41 until the ball 104 snaps into the slot 40 to retain the probe in place. The longitudinal axis of the probe shaft 92 will be perpendicular to the proximal surface 32 of the cut head and thus perpendicular to the slot 40 of the illustrative embodiment. The blade is angled to compensate for the posterior slope of the slot 40 and proximal surface 32 of the cut head 6 such that the upper surface 110 of the blade 108 is approximately horizontal when the tibia 82 is oriented vertically. The blade 108 is adjusted to a desired implant thickness setting by turning the probe knob 118 until the nut 122 is adjacent the desired mark 106.

With the base 4 of the cut guide assembly pinned to the tibia 82, the cut head 6 is adjusted up and down by turning the adjustment knob 46 until the blade 108 contacts the femur. If it is desirable to remove more or less bone from the tibia 82, the knob 116 is turned to adjust the blade up or down the shaft to the next mark 106 corresponding to a tibial implant thickness and then the cut head 6 is repositioned. The knee can be positioned in different degrees of flexion, such as zero and ninety degrees, to set the tibial cut depth. The adjustability of the blade 108 of this embodiment also makes it possible to get a direct reading in millimeters comparing the gap between the femur and tibia at different flexion angles. For example, the guide can first be set with the knee in full extension. After repositioning the knee to ninety degrees of flexion, the knob 116 can be turned to reposition the blade 108 against the bone. The difference in the flexion and extension gaps is shown by the difference between the marks 106 on the probe shaft 92 that aligned with the blade in the two knee positions.

Where the femoral bone has already been cut, as shown in the FIG. 7, the flat upper surface 110 of the blade facilitates positioning the femur 80 at flexion angles corresponding to the femoral bone cuts. For example, in extension, the distal cut surface 130 will lie flat against the blade 108. In flexion, the posterior cut surface 132 will lie flat against the blade. The blade 108 can be narrow, as shown, such that it is less than one-half the width of the femur and contacts one femoral condyle or corresponding cut surface at a time. Alternatively, the blade can be wide, such that it is greater than one-half the width of the femur, so that both condyles contact the blade at the same time. Likewise, the cut guide described above can be used with a unicondylar knee arthroplasty as well as a total knee arthroplasty.

It will be understood by those skilled in the art that the foregoing has described illustrative embodiments of the present invention and that variations may be made to these embodiments without departing from the spirit and scope of the invention defined by the appended claims. For example the illustrative embodiments depict using saw guides and blades to make the bone cuts. However, the claimed methods and cut guides could also be used with other bone removal systems to set their reference bases to achieve the desired position of the tibial resection.

What is claimed is:

1. A tibial cut guide for cutting the proximal tibia of a knee joint, including a femur and a tibia, to prepare the joint for receiving an implant, the tibial cut guide comprising:

a cutter guide including a guide surface defining a tibial cutting plane for resecting the proximal tibia;

a plurality of probes interchangeably connectable to the cutter guide, each probe extending from the cutter guide to project between the tibia and femur, each probe defining a femoral reference surface spaced a predetermined distance above the tibial cutting plane to contact a lower surface of the femur overlying the tibia and thus space the tibial cutting plane the predetermined distance from the lower surface of the femur, the predetermined spacing of the femoral reference surface from the tibial cutting plane being adjustable by interchangeably connecting each of the plurality of probes to the cutter guide, each probe being sized to space the tibial cutting plane from the femur a different distance corresponding to a different available implant thickness.

2. A tibial cut guide for cutting the proximal tibia of a knee joint, including a femur and a tibia, to prepare the joint for receiving an implant, the tibial cut guide comprising:

a cutter guide including a guide surface defining a tibial cutting plane for resecting the proximal tibia;

a probe connected to the cutter guide, the probe extending from the cutter guide to project between the tibia and femur, the probe defining a femoral reference surface spaced a predetermined distance above the tibial cutting plane to contact a lower surface of the femur overlying the tibia and thus space the tibial cutting plane the predetermined distance from the lower surface of the femur, the predetermined spacing of the femoral reference surface from the tibial cutting plane being adjustable by adjusting the probe to position the femoral reference surface at different known distances from the tibial cutting plane, the probe comprising:
an elongated shaft having a proximal end, a distal end, and a longitudinal axis from the proximal end to the distal end, the shaft including indicia corresponding to different available implant thicknesses; and
a blade defining the femoral reference surface, the blade being mounted for axial translation along the shaft between predetermined positions corresponding to the shaft indicia.

3. A tibial cut guide for cutting the proximal tibia of a knee joint, including a femur and a tibia, to prepare the joint for receiving an implant, the tibial cut guide comprising:
a cutter guide including a guide surface defining a tibial cutting plane for resecting the proximal tibia;
a probe connected to the cutter guide for up and down movement relative to the cutter guide transverse to the cutting plane, the probe extending from the cutter guide to project between the tibia and femur, the probe defining a femoral reference surface spaced a predetermined distance above the tibial cutting plane to contact a lower surface of the femur overlying the tibia and thus space the tibial cutting plane the predetermined distance from the lower surface of the femur; and
means for moving the probe up and down transverse to the cutting plane to adjust the predetermined spacing of the femoral reference surface from the tibial cutting plane, the guide surface comprising a slot defining the tibial cutting plane for guiding a saw blade and the probe engaging the slot to space the slot a known distance from the femoral reference surface.

4. A tibial cut guide for cutting the proximal tibia of a knee joint, including a femur and a tibia, to prepare the joint for receiving an implant, the tibial cut guide comprising:
a cutter guide including a guide surface defining a tibial cutting plane for resecting the proximal tibia;
a probe connected to the cutter guide, the probe extending from the cutter guide to project between the tibia and femur, the probe defining a femoral reference surface spaced a predetermined distance above the tibial cutting plane to contact a lower surface of the femur overlying the tibia and thus space the tibial cutting plane the predetermined distance from the lower surface of the femur, the predetermined spacing of the femoral reference surface from the tibial cutting plane being adjustable; and
a cut guide base, the cutter guide being adjustably mounted on the cut guide base such that the cutter guide can be adjusted up and down relative to the base, the probe further including a support having indicia on it, the femoral reference surface being adjustable up and down the support to position the reference surface adjacent each of the femoral indicia.

5. A tibial cut guide for cutting the proximal tibia of a knee joint, including a femur and a tibia, to prepare the joint for receiving an implant, the tibial cut guide comprising:
a cutter guide including a guide surface defining a tibial cutting plane for resecting the proximal tibia:
a probe connected to the cutter guide for up and down movement relative to the cutter guide transverse to the cutting plane, the probe extending from the cutter guide to project between the tibia and femur, the probe defining a femoral reference surface spaced a predetermined distance above the tibial cutting plane to contact a lower surface of the femur overlying the tibia and thus space the tibial cutting plane the predetermined distance from the lower surface of the femur, wherein the probe includes an elongated shaft having a free end defining the femoral reference surface, a first portion of the shaft extending outwardly from the cutter guide a first predetermined distance and a second portion of the shaft, adjacent the free end, being bent in a plane perpendicular to the tibial cutting plane so that the femoral reference surface angles upwardly away from the first portion of the shaft toward the femur; and
means for moving the probe up and down transverse to the tibial cutting plane to adjust the predetermined spacing of the femoral reference surface from the tibial cutting plane, the tibial cut guide including indicia corresponding to different available implant thicknesses, the indicia indicating an implant thickness corresponding to the spacing of the femoral reference surface from the tibial cutting plane.

6. A tibial cut guide for cutting the proximal tibia of a knee joint, including a femur and a tibia, to prepare the joint for receiving an implant, the tibial cut guide comprising:
a cutter guide including a guide surface defining a tibial cutting plane for resecting the proximal tibia;
a probe connected to the cutter guide, the probe extending from the cutter guide to project between the tibia and femur, the probe defining a femoral reference surface spaced a predetermined distance above the tibial cutting plane to contact a lower surface of the femur overlying the tibia and thus space the tibial cutting plane the predetermined distance from the lower surface of the femur, the predetermined spacing of the femoral reference surface from the tibial cutting plane being adjustable, the guide surface comprising a slot defining the tibial cutting plane for guiding a saw blade and the probe engaging the slot to space the slot a known distance from the reference surface, the probe comprising a body having a proximal end, a distal end, and a longitudinal axis extending between the proximal and distal ends; a probe arm extending from the body adjacent the proximal end and defining the femoral reference surface;
and an engagement tab mounted to the body adjacent the distal end, the engagement tab including a plurality of engagement ends, each end projecting outwardly from the body, each end being spaced a different axial distance from the femoral reference surface such that the tab ends may be interchangeably engaged with the slot to space the femoral reference surface different distances from the slot.

7. A tibial cut guide for cutting the proximal tibia of a knee joint, including a femur and a tibia, to prepare the joint for receiving an implant, the tibial cut guide comprising:
a cutter guide including a guide surface defining a tibial cutting plane for resecting the proximal tibia:
a probe connected to the cutter guide for up and down movement relative to the cutter guide transverse to the tibial cutting plane, the probe extending from the cutter guide to project between the tibia and femur, the probe defining a femoral reference surface spaced a predetermined distance above the tibial cutting plane to contact a lower surface of the femur overlying the tibia and thus space the tibial cutting plane the predetermined distance from the lower surface of the femur; and means for moving the probe up and down transverse to the tibial cutting plane to adjust the predetermined spacing of the femoral reference surface from the tibial cutting plane, the tibial cut guide including indicia corresponding to different available implant thicknesses, the indicia indicating an implant thickness corresponding to the spacing of the femoral reference surface from the tibial cutting plane; and a base mountable to the tibia, the cutter guide and the probe being mounted to the base for simultaneous up and down translation relative to the base, the cutter guide and the probe being simultaneously adjustable up and the down relative to the base while the spacing between the tibial cutting plane and probe remains fixed.

* * * * *